United States Patent [19]
Nickolson

[11] Patent Number: 5,977,099
[45] Date of Patent: Nov. 2, 1999

[54] PHARMACEUTICAL COMPOSITION COMPRISING MIRTAZAPINE AND ONE OR MORE SELECTIVE SEROTONIN REUPTAKE INHIBITORS

[75] Inventor: Victor Johannes Nickolson, Hermelijnendreef, Netherlands

[73] Assignee: Akzo Nobel, N.V., Arnhem, Netherlands

[21] Appl. No.: 08/876,346

[22] Filed: Jun. 16, 1997

[30] Foreign Application Priority Data

Jun. 19, 1996 [EP] European Pat. Off. .............. 96201703

[51] Int. Cl.$^6$ ........................ A61K 31/55; C07D 487/12
[52] U.S. Cl. ............................................. 514/214; 540/578
[58] Field of Search .............................. 540/578; 514/214

[56] References Cited

FOREIGN PATENT DOCUMENTS 0431663  6/1991  European Pat. Off. .
2511869  3/1983  France .

OTHER PUBLICATIONS

Davis et al., *CNS Drugs*, 5:5:389–402, May 1996.
Broekkamp, C.L.E. et al.: Prospects for improved Antidepressants. J. Med. Chem. vol. 38 (23), pp. 4615–4633, 1995.

*Primary Examiner*—John Kight
*Assistant Examiner*—Charanjit S. Aulakh
*Attorney, Agent, or Firm*—Mary E. Gormley

[57] ABSTRACT

The invention relates to a pharmaceutical composition comprising mirtazapine, a selective serotonin reuptake inhibitor (SSRI) and pharmaceutically acceptable auxiliaries. In particular the SSRI is selected from fluoxetine, fluvoxamine, citalopram, cericlamine, femoxetine, sertraline, paroxetine, ifoxetine, cyanodothiepin and litoxetine. The composition which can be used to treat depressant patients has less side effects than treatment of the patients with mirtazapine or the SSRI alone.

13 Claims, No Drawings

PHARMACEUTICAL COMPOSITION COMPRISING MIRTAZAPINE AND ONE OR MORE SELECTIVE SEROTONIN REUPTAKE INHIBITORS

The invention relates to pharmaceutical compositions comprising mirtazapine and selective serotonin reuptake inhibitors (SSRI's), to a package containing dosage units comprising mirtazapine and an SSRI, and to a method of treatment of depressive patients.

Depression is a chronic illness that affects people of all ages. Although there are many effective antidepressant agents available, the current armamentarium of treatments is often not adequate, with unsatisfactory results in about one third of all subjects treated. Of the various classes of antidepressants which are currently available, the selective serotonin reuptake inhibitors (SSRI's) are among the most successful. SSRI's have a high ratio of 5 HT reuptake inhibition over noradrenaline reuptake inhibition. SSRI's have been available since the early 1980s and the SSRI zimelidine was the first drug to be marketed. Other SSRI's on the market or under development are for example fluoxetine, fluvoxamine, citalopram, cericlamine, femoxetine, ifoxetine, cyanodothiepin, sertraline, paroxetine, and litoxetine. Although launched as new breakthrough drugs due to their favourable profiles compared to the classical antidepressant drugs which preceded them, SSRI's are considered to have many troublesome side effects. These often preclude the use of SSRI's for treatment of depression. Furthermore, some investigators believe that in the subpopulation of melancholic depressed patients SSRI's may even be inferior to other antidepressants. The most obvious side effects of SSRI's are headache, nausea, appetite inhibition and disturbance of sexual functions, such as anorgasmia and loss of libido. These side effects of sexual dysfunction can easily interfere with long term compliance.

It has now be found that administration of mirtazapine, which is one of the newest antidepressant agents and has been disclosed in U.S. Pat. No. 4,062,848, is able to prevent or at least reduce significantly the side effects occurring when SSRI's are administered.

This finding is the more surprising because mirtazapine and SSRI's share many features. Like SSRI's, mirtazapine has a low affinity for muscarinic cholinergic receptors, noradrenaline uptake carrier and alpha-1 adrenergic receptors. Further, both enhance serotonin release. In contrast to SSRI's, mirtazapine does not inhibit the neuronal uptake pump for serotonin. The most significant adverse effect of mirtazapine treatment is somnolence. An additional advantage of the present invention is that SSRI's diminish the side effects of mirtazapine when both are administered. The present invention thus concerns the administration of two different classes of antidepressant drug, each drug mutually diminishing the side effects of the other drug. It has further been found than both drugs enhance each others efficacy as antidepressant drug. As a consequence SSRI's if administered together with mirtazapine, can be used for more patients while maintaining or enhancing the therapeutic effect.

Thus according to one aspect, the present invention provides a combination comprising mirtazapine or a pharmaceutically acceptable salt thereof and one or more SSRI's or a pharmaceutically acceptable salt thereof, preferably one SSRI. Most preferably, the combination comprises mirtazapine with an SSRI. Such aforementioned combinations may hereinafter be referred to as combinations according to the invention.

It will be appreciated that the compounds of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients.

Suitable salts include acid addition salts, for example, hydrochloric, fumaric, maleic, citric or succinic acid, these acids being mentioned only by way of illustration and without implied limitation.

It will be appreciated that mirtazapine, the SSRI's and the salts thereof may contain one or more centres of chirality and exist as stereoisomers including diastereomers and enantiomers. The present invention includes the aforementioned stereoisomers within its scope and each of the individual (R) and (S) enantiomers of the compounds and their salts, substantially free, ie associated with less than 5%, preferably less than 2%, in particular less than 1% of the other enantiomer and mixtures of such enantiomers in any proportions including racemic mixtures containing substantially equal amounts of the two enantiomers.

The present invention further provides combinations according to the invention for use in therapy, more particularly in the treatment or prophylaxis of depression.

Further the invention comprises the use of combinations according to the present invention for the manufacture of a medicament having antidepressant activity with a minimum of side effects. The present invention also provides the use of mirtazapine in the manufacture of a medicament for administration concomitantly or sequentially with one or more SSRI's for the treatment of depression. It will be appreciated that an SSRI may be used in the manufacture of the above medicament for administration concomitantly or sequentially with mirtazapine.

The invention further includes the use of mirtazapine and an SSRI for the manufacture of a medicament having antidepressant activity without inducing headache, nausea, appetite inhibition, or disturbance of sexual functions.

The present invention further includes a method for the treatment of an animal, for example, a mammal including a human patient, suffering from depression, which comprises administering an effective amount of a combination according to the invention.

The method of this invention is suitable for all SSRI's. For instance mirtazapine or a pharmaceutically acceptable salt thereof can be combined with fluoxetine, fluvoxamine, citalopram, cericlamine, femoxetine, sertraline, paroxetine, ifoxetine, cyanodothiepin and litoxetine, or a pharmaceutically acceptable salt thereof. The combinations of mirtazapine with one or more of fluoxetine, fluvoxamine, citalopram, sertraline, and paroxetine are preferred. Preferred is the combination of mirtazapine or a pharmaceutically acceptable salt thereof with fluoxetine or a pharmaceutically acceptable salt thereof. Most preferred is the combination of mirtazapine with fluoxetine.

The amount of a combination of mirtazapine (or a pharmaceutically acceptable salt thereof) and an SSRI (or a pharmaceutically acceptable salt thereof), required to produce the efficacious effects will, of course, vary and is ultimately at the discretion of the medical practitioner. The factors to be considered include the route of administration and nature of the formulation, the animal's body weight, age and general condition and the nature and severity of the disease to be treated.

In general, a suitable dose of mirtazapine or a pharmaceutically acceptable salt thereof for administration to a human will be in the range of 0.01 to 30 mg per kilogram body weight of the recipient per day, preferably in the range of 0.1 to 5 mg per kilogram body weight per day and most preferably in the range of 0.3 to 1.0 mg per kilogram body weight per day.

In general, a suitable dose of an SSRI or a pharmaceutically acceptable salt thereof for administration to a human will be in the range of 0.01 to 50 mg per kilogram body weight of the recipient per day, preferably in the range of 0.1 to 3 mg per kilogram body weight per day. In the case of fluoxetine, a suitable dose will be in the range of 0.01 to 10 mg per kilogram body weight of the recipient per day, preferably in the range of 0.1 to 1 mg per kilogram body weight per day.

Unless otherwise stated all weights of active ingredients are calculated in terms of drug per se. The desired dose is preferably presented as two, three, four, five or more sub-doses administered at appropriate intervals throughout the day. These sub-doses may be administered in unit dosage forms, for example, containing 5 to 50 mg, preferably 10 mg of mirtazapine. The SSRI may be administered in unit dosage forms of 10 to 100 mg, preferably 10 to 50 mg. Fluvoxamine is conveniently administered in dosage unit forms of 50 to 100 mg, paroxetine in dosage units of 20 mg and sertraline 50 mg. In the case of fluoxetine, a typical dosage unit is 20 mg.

The components of the combination which may be referred to as active ingredients may be administered for therapy to an animal e.g. a mammal including a human in a conventional manner.

While it is possible for the active ingredients of the combination to be administered as the raw chemical it is preferable to present them as a pharmaceutical formulation. Pharmaceutical formulations according to the present invention comprise the active ingredients (that is, the combination of mirtazapine or a pharmaceutically acceptable salt thereof and one or more SSRI's or a pharmaceutically acceptable salt thereof) together with one or more pharmaceutically acceptable carriers or excipients and optionally other therapeutic agents. The carrier(s) must be acceptable in the sense of being compatible with the other ingredients of the formula and not deleterious to the recipient thereof. When the individual components of the combination are administered separately they are generally each presented as a pharmaceutical formulation.

Suitable formulations include those suitable for oral, rectal, nasal, topical (including transdermal, buccal and sublingual), vaginal or parenteral (including subcutaneous, intramuscular, intravenous and intradermal) administration. The formulations may be prepared by any methods well known in the art of pharmacy, for example, using methods such as those described in Gennaro et al., Remington's Pharmaceutical Sciences (18th ed., Mack Publishing Company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavouring agents and wetting agents.

Formulations suitable for oral administration may be presented as discrete units such as pills, tablets or capsules each containing a predetermined amount of active ingredient; as a powder or granules; as a solution or suspension. The active ingredient may also be present as a bolus or paste, or may be contained within liposomes.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

The present invention further includes a process for the preparation of a pharmaceutical formulation which comprises bringing into association a combination of mirtazapine (or a pharmaceutically acceptable salt thereof) and one or more SSRI's (or a pharmaceutically acceptable salt thereof) with one or more pharmaceutically acceptable carriers therefor.

In one embodiment a mixture of mirtazapine and one or more SSRI's may be presented as a pharmaceutical formulation in unit dosage form, for example, administered in the form of a tablet, pill, capsule and the like. Such dosage forms are known in the art, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable amounts of active ingredients are, for example, a tablet comprising 5 to 50 mg of mirtazapine and typically 5 to 100 mg of SSRI. In a specific example, a tablet comprising 15 mg of mirtazapine and 20 mg of fluoxetine is obtained. Amounts of SSRI higher than 100 mg may be necessary when SSRI's are used with low intrinsic activity.

Suitable carriers with which the compositions can be administered include lactose, starch, cellulose derivatives and the like, or mixtures thereof, used in suitable amounts.

More commonly these days pharmaceutical formulations are prescribed to the patient in "patient packs" containing the whole course of treatment in a single package, usually a blister pack. Patient packs have an advantage over traditional prescriptions, where a pharmacists divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions.

A further embodiment includes a package containing separate dosage units, one or more of which containing mirtazapine or a pharmaceutically acceptable salt thereof and one or more of which containing an SSRI or a pharmaceutically acceptable salt thereof. Dosage units containing mirtazapine (or a pharmaceutically acceptable salt thereof) have suitable amounts of active ingredient, for instance 5 to 50 mg mirtazapine, ) have for instance 10 to 30 mg of the SSRI. A package contains enough tablets, capsules or the like to treat a patient for a pre-determinded period of time, for instance for 2 weeks, 1 month or 3 months.

Patients, or course, can also be treated by using separated dosage units, each containing mirtazapine or an SSRI. Such separated dosage units are consisered to be encompassed in the presently described packages.

The present invention further includes, a patient pack comprising mirtazapine and an SSRI and an information insert containing directions on the use of the active ingredients together in combination.

Mirtazapine may be prepared using the method described in U.S. Pat. No. 4,062,843 which is incorporated herein by reference.

SSRI's may be prepared by any method known in the art. For example, fluoxetine and its pharmaceutically acceptable acid addition salts may be prepared by any method known in the art for the preparation of a compound of similar structure. Typically the compounds are prepared by the methods described in U.S. Pat. No. 4,314,081. Pharmaceutical compositions containing fluoxetine are disclosed in U.S. Pat. No. 4,194,009. The contents of U.S. Pat. Nos. 4,314,081 and 4,194,009 are incorporated herein by reference.

The invention is further illustrated by the following examples.

EXAMPLE 1

Disturbance of Sexual Functions in Rats by Fluoxetine

Male rats were individually placed in small cages. Observations were made continuously. Due to treatment of the rats with fluoxetine they have in average 2.1±0.3 spontaneous erections with ejaculations. This is according to work published by Berendsen and Broekkamp, European J Pharmacol 135:279–287 1987.

When the rats were treated with both fluoxetine and mirtazapine there is a strong and statistically significant reduction in the occurrence of penile erections. A dose of 0.1 mg/kg of mirtazapine is sufficient to antagonise this abnormal effect of fluoxetine on a sexual function:

The means were obtained from 11 rats.

Fluoxetine 22 mg/kg subcutaneously (sc): 2.1±0.3 erections

Fluoxetine 22 mg/kg sc+mirtazapine 0.1 mg/kg sc: 0.2±0.1 erections

Fluoxetine 22 mg/kg scC+mirtazapine 0.22 mg/kg sc: 0.4±0.2 erections

EXAMPLE 2

Reduction in Appetite Suppressant Effect by Fluoxetine

Rats were placed for 30 minutes in a cage were food is available which rats prefer to eat. They eat 14.5±1.8 grams (mean of 7 rats). The food consists of living mealworms.

Rats which were treated with 30 mg/kg fluoxetine sc eat only 3±0.4 grams. This is a reduction of 80%. When such a comparison was made with concomitant treatment with 2 mg/kg mirtazapine sc the reduction was only 40%. This is a clear but partial antagonism of the appetite inhibiting effect of fluoxetine by mirtazapine.

I claim:

1. A combination comprising mirtazapine or a pharmaceutically acceptable salt thereof and at least one SSRI's or a pharmaceutically acceptable salt thereof.

2. The combination according to claim 1, wherein the SSRI is one selected from the group consisting of zimeldine, fluoxetine, fluvoxamine, citalopram, cericlamine, femoxetine, ifoxetine, cyanodothiepin, sertraline, paroxetine, and litoxetine.

3. The combination according to claim 1, comprising mirtazapine and fluoxetine.

4. A pharmaceutical composition comprising an effective amount of a combination according to claim 1 in association with one or more pharmaceutically acceptable carriers therefor.

5. A method for the treatment of depression in an animal, which comprises treating said animal with a therapeutically effective amount of a combination as defined in claim 1.

6. A package containing separated dosage units, of which at least one dosage unit comprises mirtazapine and at least one other dosage unit comprises an SSRI.

7. The pharmaceutical composition according to claim 4, wherein the SSRI is at least one selected from the group consisting of zimeldine, fluoxetine, fluvoxamine, citalopram, cericlamine, femoxetine, ifoxetine, cyanodothiepin, sertraline, paroxetine, and litoxetine.

8. The pharmaceutical composition according to claim 4, comprising mirtazapine and fluoxetine.

9. The method of claim 5, wherein the at least one SSRI's in said combination are selected from the group consisting of zimeldine, fluoxetine, fluvoxamine, citalopram, cericlamine, femoxetine, ifoxetine, cyanodothiepin, sertraline, paroxetine, and litoxetine.

10. The method of claim 5, wherein the combination comprises mirtazapine and fluoxetine.

11. A method for the treatment of depression in an animal, which comprises treating said animal with a therapeutically effective amount of the pharmaceutical composition of claim 4.

12. The method of claim 11, which comprises treating said animal with a therapeutically effective amount of the pharmaceutical composition of claim 11.

13. The package according to claim 6, wherein the SSRI is fluoxetine.

* * * * *

UNITED STATES PATENT AND TRADEMARK OFFICE
CERTIFICATE OF CORRECTION

PATENT NO. : 5,977,099 Page 1 of 1
DATED : November 2, 1999
INVENTOR(S) : V. J. Nickolson It is certified that error appears in the above-identified patent and that said Letters Patent is hereby corrected as shown below:

<u>Column 6,</u>
Line 53, change "11" to -- 7 --.

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

PATENT NO.      : 5,977,099                                    Page 1 of 1
DATED           : November 2, 1999
INVENTOR(S)     : V. J. Nickolson It is certified that error appears in the above-identified patent and that said Letters Patent is hereby corrected as shown below:

Column 6,
Lines 51 and 53, change "11" to -- 7 --.

This certificate supersedes Certificate of Correction issued January 7, 2003.

Signed and Sealed this

Fifteenth Day of April, 2003

JAMES E. ROGAN
*Director of the United States Patent and Trademark Office*